United States Patent
Ronn

[19]

[11] Patent Number: 5,944,707
[45] Date of Patent: Aug. 31, 1999

[54] ABSORBENT ARTICLE HAVING AN ADJUSTMENT SYSTEM

[75] Inventor: Karl P. Ronn, Cincinnati, Ohio

[73] Assignee: The Procter & Gamble Company, Cincinnati, Ohio

[21] Appl. No.: 08/933,326

[22] Filed: Sep. 18, 1997

Related U.S. Application Data

[63] Continuation of application No. 08/588,487, Jan. 18, 1997, abandoned.

[51] Int. Cl.$^6$ ....................................... A61F 13/15
[52] U.S. Cl. ....................... 604/386; 604/385.1; 604/390
[58] Field of Search ................................ 604/385.1–387, 604/389, 390, 391

[56] References Cited

U.S. PATENT DOCUMENTS

| | | | |
|---|---|---|---|
| 2,294,617 | 9/1942 | Horowitz | 604/386 |
| 2,649,858 | 8/1953 | Bolt | 604/389 |
| 2,839,347 | 5/1958 | Connelly | 604/385.1 |
| 3,776,232 | 12/1973 | Schaar | 604/385.1 |
| 3,913,578 | 10/1975 | Schaar | 604/385.1 |
| 4,475,912 | 10/1984 | Coates | 604/385.1 |
| 4,753,650 | 6/1988 | Williams | 604/389 |
| 4,801,298 | 1/1989 | Sorenson et al. | 604/384 |
| 4,826,499 | 5/1989 | Ahr | 604/389 |
| 4,850,990 | 7/1989 | Huntoon et al. | 604/385.2 |
| 4,883,481 | 11/1989 | Blanchard | 604/385.2 |
| 4,936,840 | 6/1990 | Proxmire | 604/385.2 |
| 4,963,140 | 10/1990 | Robertson et al. | 604/389 |
| 4,981,480 | 1/1991 | Gaudet et al. | 604/386 |
| 5,024,672 | 6/1991 | Widlund | 604/390 |
| 5,261,901 | 11/1993 | Guay | 604/391 |
| 5,370,634 | 12/1994 | Ando et al. | 604/385.1 |
| 5,374,262 | 12/1994 | Keuhn, Jr. et al. | 604/391 |
| 5,489,282 | 2/1996 | Zehner et al. | 604/385.1 |
| 5,531,732 | 7/1996 | Wood | 604/385.2 |

FOREIGN PATENT DOCUMENTS

| | | | |
|---|---|---|---|
| 0623330 | 11/1994 | European Pat. Off. | 604/389 |
| 0 858 787 A1 | 8/1998 | European Pat. Off. | |
| 2267024 | 11/1993 | United Kingdom | 604/396 |

*Primary Examiner*—Mark O. Polutta
*Attorney, Agent, or Firm*—David M. Weirich; Thomas J. Osborne, Jr.; Theodore P. Cummings

[57] ABSTRACT

The present invention provides an absorbent article having an adjustment system optimally placed on the backsheet and/or the topsheet to provide the absorbent article with an adjustable fit. Once the absorbent article is fitted about a wearer, the adjustment system may be adjusted to securely fit the absorbent article about a wearer's waist and legs, thus reducing the opportunities for leakage of bodily fluids.

11 Claims, 4 Drawing Sheets

ABSORBENT ARTICLE HAVING AN ADJUSTMENT SYSTEM

This is a continuation of application Ser. No. 08/588,487, filed on Jan. 18, 1997, abandoned.

FIELD OF THE INVENTION

The present invention relates to absorbent articles such as diapers, incontinence briefs, training pants, and the like, and more particularly, to absorbent articles having an adjustment system that improves the fit as well as the containment characteristics of the absorbent article.

BACKGROUND OF THE INVENTION

Infants and other incontinent individuals wear absorbent articles such as diapers to receive and contain urine and other body exudates. Absorbent articles function both to contain the discharged materials and to isolate these materials from the body of the wearer and from the wearer's garments and bed clothing. Disposable absorbent articles having many different basic designs are known to the art. For example, U.S. Pat. No. Re. 26,152, entitled "Disposable Diaper" issued to Duncan and Baker on Jan. 31, 1967, describes a disposable diaper which has achieved wide acceptance and commercial success. U.S. Pat. No. 3,860,003, entitled "Contractible Side Portions For Disposable Diaper", issued to Buell on Jan. 14, 1975, describes an elasticized leg cuff disposable diaper which has achieved wide acceptance and commercial success.

However, absorbent articles have a tendency to sag or gap away from and to slide/slip down on the body of the wearer during wear. This sagging/gapping and sliding/slipping is caused by the relative motions of the wearer as the wearer breathes, moves and changes positions, by the downward forces generated when the absorbent article is loaded with body exudates, and by the deformation of the materials of the absorbent article itself when subjected to such wearer's motions. This sagging/gapping and sliding/slipping of the absorbent article can lead to premature leakage and poor fit of the absorbent article about the wearer particularly in the waist regions and the leg regions of the absorbent article.

Therefore, it is an object of the present invention to provide an absorbent article having an adjustment system which allows the absorbent article to be adjusted to the shape and size of the wearer.

It is a further object to provide an absorbent article with improved containment characteristics particularly at the waist and leg openings.

These and other objects of the present invention will be more readily apparent when considered in reference to the following description and when taken in conjunction with the accompanying drawings.

SUMMARY OF THE INVENTION

The present invention provides an absorbent article having a first waist region, a second waist region longitudinally opposed to the first waist region, a crotch region positioned between the first waist region and the second waist region, longitudinal edges, end edges, an outer surface, and an inner surface. The absorbent article comprises a containment assembly comprising a liquid pervious topsheet, a liquid impervious backsheet joined to the topsheet, and an absorbent core positioned between the topsheet and the backsheet. The absorbent article also comprises a fastening system disposed on the absorbent article for providing a side closure which maintains the first waist region and the second waist region in an overlapping configuration. The fastening system comprises a securement member disposed adjacent to each of the longitudinal edges in the second waist region and a landing member disposed in the first waist region. The landing member is engageable with the securement members. Additionally, the absorbent article comprises an adjustment system for providing improved fit which has a longitudinal axis and a transverse axis. The adjustment system comprises at least one adjustment tab being disposed on the absorbent article. The adjustment tab has a fixed portion that is secured to the absorbent article, an intermediate portion connected to the fixed portion, and a grasping portion that is connected to the intermediate portion. Furthermore, the intermediate portion and the grasping portion are preferably connected by a fold line which allows the grasping portion to be folded upward away from the outer surface and therefore readily grasped by a diaperer.

In a preferred embodiment, at least one adjustment system is disposed on the outer surface of the absorbent article. Preferably at least one adjustment system is disposed in the first waist region, the second waist region or both.

In a preferred embodiment, the adjustment system comprises a release portion having a fixed surface opposed to an attachment surface. The adjustment tab fits on and is releasably attached to the attachment surface of the release portion. The fixed surface of the release portion is fixedly attached to the absorbent article. Preferably, the fixed surface of the release portion and the fixed portion of the adjustment tab are fixedly attached to the outer surface of the backsheet. The adjustment tab and the release portion are releasably attached to one-another by an adhesive layer. Alternatively, the adjustment tab and the release portion are releasably attached to one-another using hooks and loops.

An alternative embodiment provides for an absorbent article having a first waist region, a second waist region longitudinally opposed to the first waist region, a crotch region positioned between the first waist region and the second waist region, longitudinal edges, end edges, an outer surface, and an inner surface. The absorbent article provides a containment assembly comprising a liquid pervious topsheet, a liquid impervious backsheet joined to the topsheet, and an absorbent core positioned between the topsheet and the backsheet. The absorbent article also comprises a fastening system disposed on the absorbent article for providing a side closure which maintains the first waist region and the second waist region in an overlapping configuration. The fastening system comprises a securement member disposed adjacent to each of the longitudinal edges in the second waist region and a landing member disposed in the first waist region. The landing member is engageable with the securement members. Additionally, the absorbent article comprises at least one adjustment system that is disposed on the absorbent article and has a longitudinal axis and a transverse axis. The adjustment system comprises a tab housing and an adjusting portion. The tab housing comprises a front end, a back end, a top surface, a bottom surface, and an opening having two edges. The adjusting portion comprises a rear end, an extension member connected to the rear end, and a head portion connected to the extension member. The rear end is secured to the absorbent article adjacent to the back end of the tab housing, and the extension member extends from the rear end through the opening to the head portion. The tab housing is constricted by pulling the head portion in a direction along the longitudinal axis. Preferably, the tab housing and adjusting portion comprise at least one type of thermoplastic material from the group consisting of linear low and medium polyethylene copolymers and high density polyethylene.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinence briefs, training pants, feminine hygiene garments, and the like.

Figure 1:
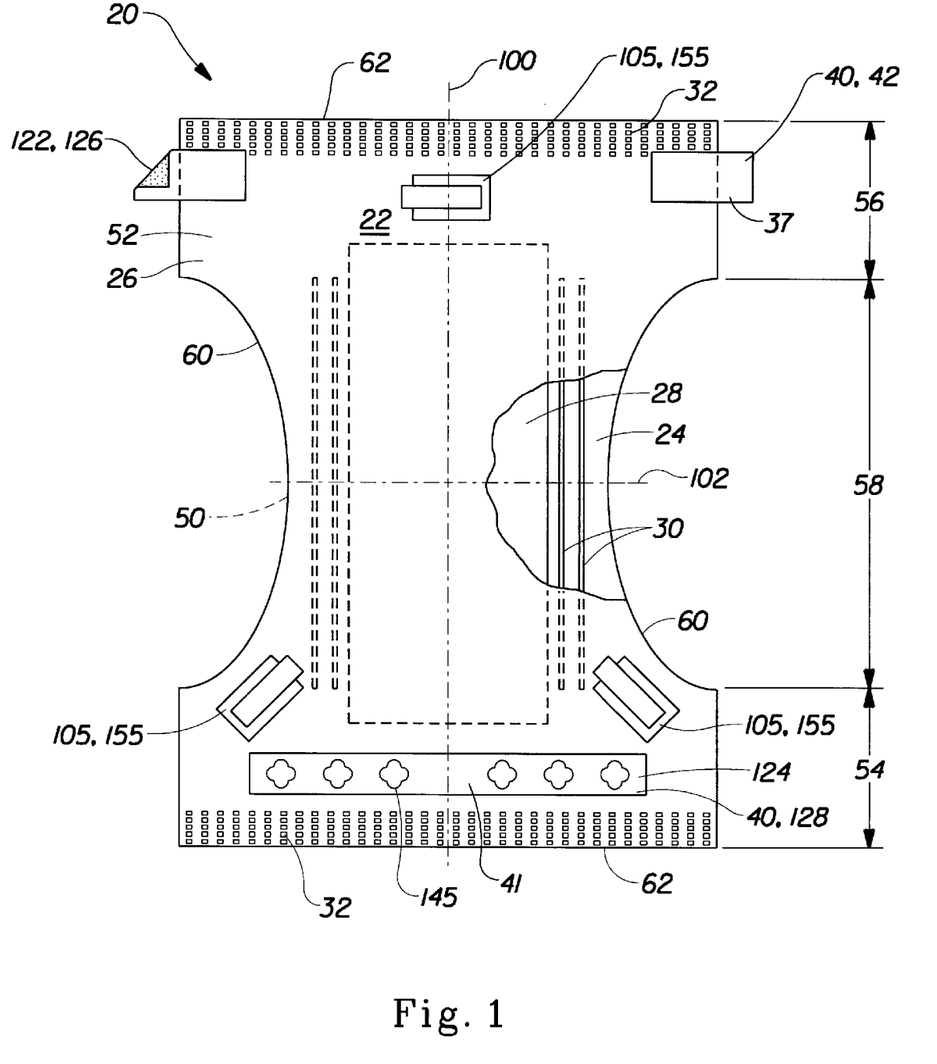
FIG. 1 is a plan view of a disposable diaper embodiment of the present invention having portions cut-away to reveal underlying structure, the outer surface of the diaper facing the viewer.

FIG. 1 is a plan view of the diaper 20 of the present invention in its flat-out, uncontracted state (i.e., with elastic induced contraction pulled out) with portions of the structure being cut-away to more clearly show the construction of the diaper 20 and with the portion of the diaper 20 which faces away from the wearer, the outer surface 52, facing the viewer. As shown in FIG. 1, the diaper 20 comprises a containment assembly 22 preferably comprising a liquid pervious topsheet 24, a liquid impervious backsheet 26 joined to the topsheet 24, and an absorbent core 28 positioned between the topsheet 24 and the backsheet 26. The diaper preferably further comprises elasticized leg cuffs 30; elasticized waistbands 32; a fastening system 40; and an adjustment system 105.

The diaper 20 is shown in FIG. 1 to have an outer surface 52 (facing the viewer in FIG. 1), an inner surface 50 opposed to the outer surface 52, a front waist region 54, a rear waist region 56 longitudinally opposed to the front waist region 54, a crotch region 58 positioned between the front waist region 54 and the rear waist region 56, and a periphery which is defined by the outer perimeter or edges of the diaper 20 in which the longitudinal edges are designated 60 and the end edges are designated 62. The inner surface 50 of the diaper 20 comprises that portion of the diaper 20 which is positioned adjacent to the wearer's body during use (i.e., the outer surface 52 is generally formed by at least a portion of the backsheet 26 and other components joined to the backsheet 26). As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. The front waist region 54 and the rear waist region 56 extend from the end edges 62 of the periphery to the crotch region 58.

The diaper 20 also has two centerlines, a longitudinal centerline 100 and a transverse centerline 102. The term "longitudinal", as used herein, refers to a line, axis, or direction in the plane of the diaper 20 that is generally aligned with (e.g., approximately parallel with) a vertical plane which bisects a standing wearer into left and right halves when the diaper 20 is worn. The terms "transverse" and "lateral", as used herein, are interchangeable and refer to a line, axis or direction which lies within the plane of the diaper that is generally perpendicular to the longitudinal direction (which divides the wearer into front and back body halves.)

The containment assembly 22 of the diaper 20 is shown in FIG. 1 as comprising the main body (chassis) of the diaper 20. The containment assembly 22 comprises at least an absorbent core 28 and preferably an outer covering layer comprising the topsheet 24 and the backsheet 26. When the absorbent article comprises a separate holder and a liner, the containment assembly 22 generally comprises the holder and the liner (i.e., the containment assembly 22 comprises one or more layers of material to define the holder while the liner comprises an absorbent composite such as a topsheet, a backsheet, and an absorbent core.) For unitary absorbent articles, the containment assembly 22 comprises the main structure of the diaper with other features added to form the composite diaper structure. Thus, the containment assembly 22 for the diaper 20 generally comprises the topsheet 24, the backsheet 26, and the absorbent core 28.

FIG. 1 shows a preferred embodiment of the containment assembly 22 in which the topsheet 24 and the backsheet 26 have length and width dimensions generally larger than those of the absorbent core 28. The topsheet 24 and the backsheet 26 extend beyond the edges of the absorbent core 28 to thereby form the periphery of the diaper 20. While the topsheet 24, the backsheet 26, and the absorbent core 28 may be assembled in a variety of well known configurations, preferred diaper configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge", which issued to Kenneth B. Buell et al on Sep. 29, 1992; each of which is incorporated herein by reference.

The absorbent core 28 may be any absorbent material which is generally compressible, conformable, non-irritating to the wearers skin, and capable of absorbing and retaining liquids and certain body exudates. The absorbent core 28 may be manufactured in a wide variety of sizes and shapes (e.g., rectangular, hourglass, asymmetric, etc.) and from a wide variety of liquid absorbent materials commonly used in disposable diapers and other absorbent articles, such as comminuted wood pulp which is generally referred to as airfelt. Examples of other suitable absorbent materials include creped cellulose wadding, absorbent foams, absorbent sponges, superabsorbent polymers, absorbent gelling materials, or any equivalent materials or combination of materials.

The configuration and construction of the absorbent core 28 may vary (e.g., the absorbent core may have varying caliper zones, a hydrophilic gradient, a superabsorbent gradient, or lower average density and lower average basis weight acquisition zones; or may comprise one or layers or structures.) Further, the absorbent capacity of the absorbent core 28 may also be varied to accommodate wearers ranging from infants through adults. However, the total absorbent capacity of the absorbent core 28 should, however, be compatible with the design exudate loading and the intended use of the diaper 20.

Exemplary absorbent structures for use in the absorbent core 28 are described in U.S. Pat. No. 4,610,678 entitled "High-Density Absorbent Structure" which issued to Paul T. Weisman and Steven A. Goldman on Sep. 9, 1986; U.S. Pat. No. 5,234,423 entitled "Absorbent Article With Elastic Waist Feature and Enhanced Absorbency", issued to Alemany et al. on Aug. 10, 1993; U.S. Pat. No. 5,217,445 entitled "Absorbent Structures Containing Superabsorbent Material and Web of Wetlaid Stiffened Fibers" issued to Young et al. on Jun. 8, 1993; U.S. Pat. No. 5,137,537 entitled "Absorbent Structure Containing Individualized, Polycarboxylic Acid Crosslinked Wood Pulp Cellulose Fibers", issued to Herron et al., on Aug. 11, 1992; U.S. Pat. No. 5,180,622 entitled "Absorbent Members Containing Interparticle Crosslinked Aggregates", issued to Berg et al., on Jan. 19, 1993; U.S. Pat. No. 5,260,345 entitled "Absorbent Foam Materials for Aqueous Body Fluids and Absorbent Articles Containing Such Materials" issued to DesMarais et al., on Nov. 9, 1993; U.S. Pat. No. 4,673,402 entitled "Absorbent Article With Dual-Layered Cores" which issued to Paul T. Weisman, Dawn I. Houghton and Dale A. Gellert on June 16. All of these patents are incorporated herein by reference.

The backsheet 26 is positioned adjacent the absorbent core 28 adjacent the surface that faces away from the wearer and is preferably secured thereto by attachment means such as those well known in the art. For example, the backsheet 26 may be secured to the absorbent core 28 by a uniform continuous layer of adhesive, a patterned layer of adhesive, or an array of separate lines, spirals, or spots of adhesive. An adhesive which has been found to be satisfactory is manufactured by H. B. Fuller Company of St. Paul Minn. and marketed as HL-1258. The attachment means preferably comprises an open pattern network of filaments of adhesive is shown in U.S. Pat. No. 4,573,986 entitled "Disposable Waste-Containment Garment", which issued to J. A. Minetola and David R. Tucker on Mar. 4, 1986, and which is incorporated herein by reference. Another suitable attachment means comprising several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Zieckler, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids and is preferably manufactured from a thin plastic film, although other flexible liquid impervious materials may also be used. As used herein, the term "flexible" refers to materials which are compliant and which will readily conform to the general shape and contours of the human body. The backsheet 26 prevents the exudates absorbed and contained in the absorbent core 28 from wetting articles which contact the diaper 20 such as bed sheets and undergarments. Further, the backsheet 26 may permit vapors to escape from the absorbent core 28 while still preventing exudates from passing through the backsheet 26. The backsheet 26 may thus comprise a woven or nonwoven material, polymeric film such as thermoplastic films of; for example, polyethylene or polypropylene, or composite materials such as film-coated nonwoven materials. Alternatively, the backsheet 26 may comprise a laminate of a nonwoven layer and a polymeric film, including embodiments wherein the nonwoven layer extends beyond the dimensions of the polymeric film. An exemplary backsheet 26 is a polyethylene film having a thickness of from about 0.012 mm (0.5 mil) to about 0.051 cm (2.0 mils). A suitable polyethylene film is manufactured by Tredegar Film Products, Inc. of Terra Haute, Ind., and is marketed in the trade as Tredegar X8526. The backsheet 26 is preferably embossed and/or matte finished to provide a more cloth like appearance.

The topsheet 24 is compliant, soft feeling, and non-irritating to the wearer's skin. Further, the topsheet 24 is liquid pervious permitting liquids to readily penetrate through its thickness. A suitable topsheet may be manufactured from a wide range of materials, such as porous foams, reticulated foams, formed films, apertured plastic films, natural fibers (e.g., wood or cotton fibers), synthetic fibers (e.g., polyester or polypropylene fibers) or from a combination of natural and synthetic fibers. There are a number of manufacturing techniques which may be used to manufacture the topsheet 24. For example, the topsheet 24 may be woven, non-woven, spunbonded, carded, or the like. One preferred topsheet 24 comprises staple length polypropylene fibers having a denier of about 2.2, such as P-8, manufactured by Veratec, Inc., a Division of the International Paper Company, of Walpole, Mass. As used herein, the term "staple length fibers" refers to those fibers having a length of at least about 15.9 mm (0.625 inches). A preferred topsheet 24 is carded, and thermally bonded by means well known to those skilled in the fabrics art.

In a preferred embodiment, the topsheet 24 is made of a hydrophobic material to isolate the wearer's skin from liquids in the absorbent core 28. If the topsheet 24 is made of a hydrophobic material, at least the upper surface of the topsheet 24 is treated to be hydrophilic so that liquids will transfer through the topsheet 24 more rapidly. This diminishes the likelihood that body exudates will flow off the topsheet 24 rather than being drawn through the topsheet 24 and being absorbed by the absorbent core 28. The topsheet 24 can be rendered hydrophilic by treating it with a surfactant including spraying the topsheet 24 material with a surfactant or immersing the material into the surfactant. A more detailed discussion of such a treatment is contained in U.S. Pat. No. 4,988,344 entitled "Absorbent Articles with Multiple Layer Absorbent Layers" issued to Reising et al., on Jan. 29, 1991, and U.S. Pat. No. 4,988,345 entitled "Absorbent Articles with Rapid Acquiring Absorbent Cores" issued to Reising on Jan. 29, 1991, each of which is incorporated herein by reference.

The topsheet 24 and the backsheet 26 may be joined together in any suitable manner as is well known in the diaper manufacturing art. As used herein, the term "joined" encompasses configurations whereby the topsheet 24 is directly joined to the backsheet 26 by affixing the topsheet 24 directly to the backsheet 26, and configurations whereby the topsheet 24 is indirectly joined to the backsheet 26 by affixing the topsheet 24 to intermediate members which in turn are affixed to the backslid 26. In a preferred embodiment, the topsheet 24 and the backsheet 26 are joined directly to each other in the diaper periphery by attachment means such as an adhesive or any other attachment means as is known in the art. Suitable attachment means are described with respect to joining the backsheet to the absorbent core.

In a preferred embodiment of the present invention, an acquisition layer(s) may be positioned between the topsheet 24 and the absorbent core 28. The acquisition layer may serve several functions including improving wicking of exudates over and into the absorbent core. There are several reasons why the improved wicking of exudates is important, including providing a more even distribution of the exudates throughout the absorbent core and allowing the diaper 20 to be made relatively thin. (The wicking referred to herein may encompass the transportation of liquids in one, two or all directions (i.e., in the x-y plane and/or in the z-direction). The acquisition layer may be comprised of several different materials including nonwoven or woven webs of synthetic fibers including polyester, polypropylene, or polyethylene; natural fibers including cotton or cellulose; blends of such fibers; bicomponent fibers; or any equivalent materials or combinations of materials. Examples of absorbent articles disclosed herein having an acquisition layer and a topsheet 24 are more fully described in U.S. Pat. No. 4,950,264 issued to Osborn and U.S. patent application Ser. No. 07/944,764, "Absorbent Article Having Fused Layers", filed Oct. 7, 1992, in the names of Cree, et al. Each of these references are incorporated herein by reference. In a preferred embodiment, the acquisition layer may be joined with the topsheet by any of the conventional means for joining webs together, most preferably by fusion bonds.

Figure 5:
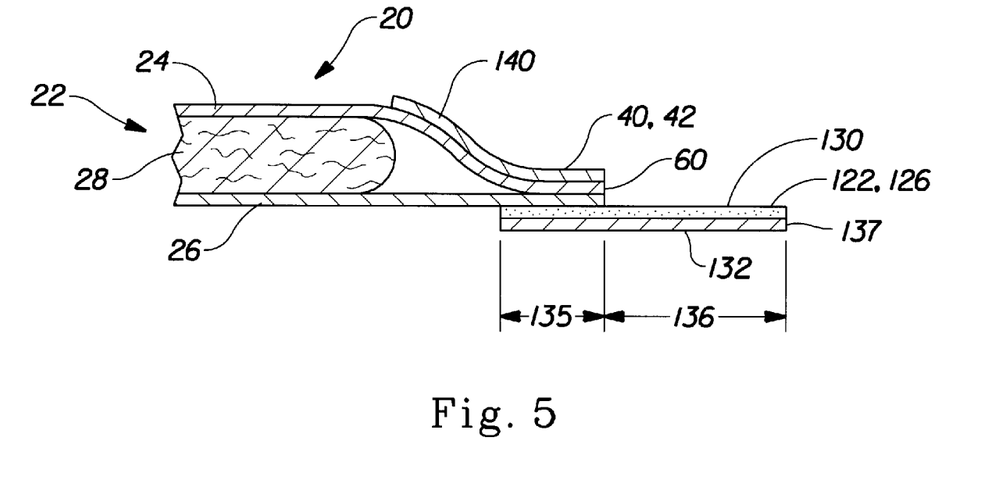
FIG. 5 is a side view of a tape tab of the present invention.

The diaper 20 also comprises a fastening system 40 which forms a side closure which maintains the front waist region 54 and the rear waist region 56 in an overlapping configuration such that lateral tensions are maintained around the circumference of the diaper to maintain the diaper on the wearer. As shown in FIG. 1, the fastening system 40 comprises a securement member 37 disposed adjacent each longitudinal edge 60 in the rear waist region 56, and at least one landing member 41 disposed in the front waist region 54 so as to form a portion of the outer surface 52. Each securement member 37 preferably comprises a tape tab 42 and a first fastening component 122 as seen in FIGS. 1 and 5. The landing member 41 preferably comprises a complimentary second fastening component 124 engageable with the first fastening component 122 of the securement member 37. An exemplary fastening system wherein the first and second fastening components each comprise mechanical closure elements comprising hook and loop fastening materials is disclosed in U.S. Pat. No. 4,869,724 issued to Scripps on Sep. 26, 1989. The fastening systems utilizing mechanical closure elements are also disclosed in U.S. Pat. No. 4,846,815 issued to Scripps on Jul. 11, 1989; and U.S. Pat. No. 4,894,060 issued to Nestegard on Jan. 16, 1990. A fastening system having combination adhesive/mechanical closure elements as described in U.S. Pat. No. 4,946,527 issued to Battrell on Aug. 7, 1990. Each of these patents are incorporated herein by reference. In a preferred embodiment of the present invention as is shown in FIG. 1, the fastening system 40 comprises an adhesive tape tab fastening system comprising a tape tab 42 having an adhesive attachment layer 126 and a landing member 41 comprising a reinforcing strip 128 joined to the backsheet 26. Examples of such adhesive tape tab fastening systems are disclosed in U.S. Pat. No. 3,848,594 issued to Buell on Nov. 19, 1974; and the adhesive tape tabs, reinforcing strip, and indicia means disclosed in U.S. Pat. No. 4,662,875 issued to Hirotsu and Robertson on May 5, 1987. Each of these patents are incorporated herein by reference.

Each securement member 37 of the fastening system 40 is intended to provide a fastening means for engaging the landing member 41 so as to provide a secure, preferably a variable positioning side closure for the diaper 20. Thus, the securement member 37 comprises at least one fastening component. Each securement member 37 also preferably comprises a means for positioning the fastening component adjacent the landing member 41 so as to achieve an optimum fitting side closure. Thus, the securement member 37 may comprise any of the well known configurations and means for achieving a side closure on a diaper such as a patch or strip of a fastening component disposed to form a portion of the inner surface of the diaper or a tape tab having a fastening component positioned thereon.

As shown in FIG. 1, each securement member 37 preferably comprises a tape tab 42. Any of the well known configurations and constructions of a tape tab may be used in the present invention. For example, an exemplary tape tab is described in detail in U.S. Pat. No. 3,848,594 issued to Buell on Nov. 19, 1974, and which patent is incorporated herein by reference. A particularly preferred tape tab 42 illustrated in FIG. 5 has a fastening surface 130 and a backing surface 132. The fastening surface 130 is that surface of the tape tab 42 designed to engage the landing member 41 of the present invention. Thus, the fastening surface 130 of the tape tab 42 is generally oriented to face the inner surface of the diaper 20. The backing surface 132 is that surface opposed to the fastening surface 130 and generally faces the outer surface of the diaper 20. The backing surface 130 is thus generally exposed during wear of the diaper 20. The preferred tape tab 42 illustrated in FIG. 5 is joined to the backsheet 26 to create a fixed portion 135 (i.e., that end of the tape tab 42 joined to the diaper 20 during manufacture). The tape tab 42 has another element which is the tab portion 136 (i.e., that end of the tape tab 42 that extends outwardly beyond the longitudinal edge 60 of the diaper 20 and that is grasped by the diaperer in securing the diaper on the wearer). The distal edge 137 of the tape tab 42 preferably has rounded corners to eliminate the possibility of harsh corner edges contacting the wearer's skin so as to prevent stomach redmarking. The preferred tape tab 42 of the present invention also comprises a release portion 140 joined to the topsheet 24 of the diaper 20. The release portion 140 allows the tab portion 136 to be inwardly folded during manufacture to protect the adhesive attachment layer 126 from contamination or de-lamination prior to use. As shown in FIG. 5, the release portion 140 extends inwardly from the longitudinal edge 60 of the diaper 20. The tab portion 136 is also preferably shorter in the lateral direction (width) than the release portion 140 so that it is easier for the diaperer to initially grasp the tab portion 136.

The fastening component of the securement member 37 forms a closure between the securement member and the complimentary fastening component of the landing member 41. Thus, the fastening component provides a means for engaging the complimentary fastening component of the landing member 41 to maintain the front waist region 54 and the rear waist region 56 in an overlapping configuration to provide a secure side closure for the diaper 20. Further, it is preferred that a diaper fit a range of different size wearers and that the fastening system be simple and easy to use. Therefore, the fastening components should allow for variable positioning of the zone of closure so that the diaper may fit a range of sizes while also being simple to fasten with minimal effort. The fastening components thus comprise any of the well known attachment means for achieving an adjustable positioning secure closure as defined hereinafter. Examples of such adjustable positioning attachment means include an adhesive attachment layer such as a pressure-sensitive adhesive as are known in the at, a mechanical closure element such as a hook fastening material or a loop fastening material, any cohesive materials as are known in the art, or a combination of an adhesive/mechanical closure element.

The first fastening component 122 is preferably a separate material, such as an adhesive attachment layer or a mechanical closure element, positioned on and joined to the tape tab 42. As shown in FIG. 4, the first fastening component 122 preferably comprises an adhesive attachment layer 126 coated on the tab portion 136 to form the fastening surface 130.

The first fastening component 122 may be positioned anywhere on the securement member 37. When the securement member 37 comprises a tape tab 42, the first fastening component 122 is preferably positioned either on all or at least a portion of the fastening surface 130 of the tab portion 136. The first fastening component 122 may comprise a combination adhesive/mechanical closure element having an adhesive attachment layer and a mechanical closure element disposed on another area of the tab portion 136 on the fastening surface 130 and adjacent the distal edge 137 of the tape tab 42. An exemplary embodiment of this configuration is disclosed in U.S. Pat. No. 4,869,724 issued to Scripps on Sep. 26, 1989, which is incorporated herein by reference.

The landing member 41 of the fastening system 40 provides a means for securing itself to the securement member 37 to provide a side closure and to maintain the front waist region 54 and the rear waist region 56 in an overlapping configuration. The landing member 41 may be disposed anywhere on the diaper 20 so long as it can engage the securement member 37 so as to provide the side closure, and preferably a variable positioning side closure. Because the landing member 41 determines the approximate location of where the securement member 37 should be placed for optimum fit, the landing member 41 is preferably positioned so as to achieve variable positioning of the side closure 50 that the diaper may fit a range of sizes, so that an overlap between the front waist region 54 and the rear waist region 56 is achieved. The landing member 41 is preferably centered about the longitudinal centerline 100 in the front waist region 54 and extends laterally outwardly.

The landing member 41 may either be a discreet, separate element or elements joined to the diaper 20 or a unitary piece of material with an element of the diaper 20. The landing member 41 may thus comprise, for example, the topsheet 24 or the backsheet 26. While the landing member 41 can assume varying sizes and shapes, it preferably comprises one or more patches of material joined to the backsheet 26 in the front waist region 54 that allows for maximum fit adjustment of diaper 20 to the wearer. In a preferred embodiment of the diaper 20, as illustrated in FIG. 1, the landing member 41 has an elongate, rectangular shape and is secured to the backsheet 26 in the front waist region 56 by an adhesive attachment means (not shown). The landing member 41 comprises a fastening component (second fastening component 124) engageable with the fastening component of the securement member 37 (first fastening component 122). Thus, the fastening component of the landing member 41 (second fastening component 124) may be manufactured from a wide range of materials and configurations capable of securely engaging the fastening component of the securement member 37 (first fastening component 122).

When the first fastening component 122 of securement member 37 comprises an adhesive attachment layer 126, the second fastening component 124 of the landing member 41 preferably comprises a reinforcing strip 128. When the first fastening component 122 of the securement member 37 comprises a mechanical closure element, a second fastening component 124 also comprises a mechanical closure element. Thus, when the first fastening component 122 comprises a hook fastening material, the second fastening component 124 preferably comprises a loop fastening material.

In a preferred embodiment of the present invention, the landing member 41 preferably comprises a reinforcing strip 128 releasably engageable with the adhesive attachment layer 126 of the tape tabs 42. The reinforcing strip 128 may comprise any number of configurations and materials secured to the backsheet 26 of the diaper 20. The reinforcing strip 128 is preferably a separate member secured to the backsheet 26 to form a portion of the outer surface 52 of the diaper 20. A preferred reinforcing strip 128 comprises a sheet of bi-axially oriented polypropylene film.

The reinforcing strip 128 is also preferably provided with indicia means 145 for aiding the diaperer in fitting the diaper to a wearer to obtain optimal waist fit and leg opening fit. The indicia means 145 may be any type of lines, patterns, ornamental designs, symbols, script, color codes, or other markings which have the capability, either inherently or with additional denotation, to aid an individual fitting the diaper to the wearer to promptly locate the desired affixation points for a particular tape tab fastener. Such indicia means 145 are more fully described in U.S. Pat. No. 4,662,875 issued to Hirotsu and Robertson on May 5, 1987, and which is incorporated herein by reference.

The diaper 20 preferably further comprises elasticized waist bands 32 that help provide improved fit and containment. The elasticized waistband 32 is that portion or zone of the diaper which is intended to elastically expand and contract to dynamically fit the wearer's waist. The elasticized waistband preferably extends longitudinally outwardly from the chassis assembly, preferably a respective waist edge of the absorbent core 28, and generally forms at least a portion of the end edge 62 of the diaper 20. While a disposable diaper of the present invention is constructed with an elasticized waistband disposed in each waist region diapers may be constructed with a single elasticized waistband. The elasticized waistband may be constructed as a separate element joined to the chassis assembly 22 or as an extension of other elements of the diaper such as the backsheet 26, the topsheet 24, or both. The elasticized waistband maybe constructed in a member of different configurations including those described in U.S. Pat. No. 4,515,595, issued to Kievit et al. on May 7, 1985, and U.S. Pat. No. 5,151,092 issued to Buell et al. on Sep. 29, 1992, each of which is incorporated herein by reference.

The diaper 20 preferably further comprises elasticized leg cuffs 30 for providing improved containment of liquids and other body exudates. Each elasticized leg cuff 30 may comprise several different embodiments for reducing the leakage of body exudates in the leg regions. (The leg cuff can be and is sometimes also referred to as leg bands, leg flaps, barrier cuffs, or elastic cuffs.) U.S. Pat. No. 3,860,003 entitled "Contractible Side Portions For a Disposable Diaper" issued to Buell on Jan. 14, 1975, describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz & Blaney on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinent garment having side-edge-leakage-guard gutters configured to contain free liquids within the garment. U.S. Pat. No. 5,032,120 entitled "Disposable Absorbent Article Having Improved Leg Cuffs" issued to Freeland & Allen on Jul. 16, 1991, discloses an absorbent article having leg cuffs having a relatively low ultimate contact force at relatively high elongation's accomplished, for example, by low contact force differential material. U.S. Pat. No. 5,087,255 entitled "Absorbent Article Having Inflected Barrier Cuffs" issued to Sims on Feb. 11, 1992, discloses an absorbent article having inflected barrier cuffs with the distal edge positioned outboard of the proximal edge in one waist region and inboard in the other to provide better fit about the hips/buttocks. Each of these patents are incorporated herein by reference.

The diaper 20 is also preferably provided with an adjustment system 105 for substantially eliminating any sagging/ gapping and sliding/slipping of the diaper. After the diaper has been placed on a wearer and the fastening system has been secured, the diaper may sag or gap away from and slip/slide down on the body of the wearer during wear. This sagging/gapping and sliding/slipping is caused by the relative motion between the diaper and the wearer as the wearer breathes, moves and changes position, and by the downward forces generated when the diaper is loaded with body exudates. This sagging/gapping and sliding/slipping of the diaper can lead to leaking of exudates from the diaper and poor fit of the diaper about the wearer. Sagging/gapping of the diaper is substantially eliminated by the adjustment system 105 as portions of the diaper which may sag or gap may be drawn or gathered to snugly fit against the body of the wearer. Sliding/slipping is thereby reduced as the diaper fits more snugly against the wearer. Thus, the adjustment system 105 provides improved fit. Additionally, as the adjustment system 105 reduces the incidence of sagging and gapping of the diaper 20 by providing a more snug fit, the incidence of exudate leakage from the diaper 20 is also reduced.

While the adjustment system 105 may comprise a number of configurations, it preferably comprises at least one adjustment tab 155. As shown in FIG. 1, the adjustment system 105 comprises a pair of adjustment tabs 155 disposed in the front waist region 54 and a single adjustment tab 155 disposed in the rear waist region 56. The adjustment tabs 155 disposed in the front waist region 54 are so placed to provide added fit and securement about a wearer's legs. The single adjustment tab 155, being disposed in the rear waist region 56, is placed at the waist to provide added fit and securement about a wearer's waist.

Figure 2:
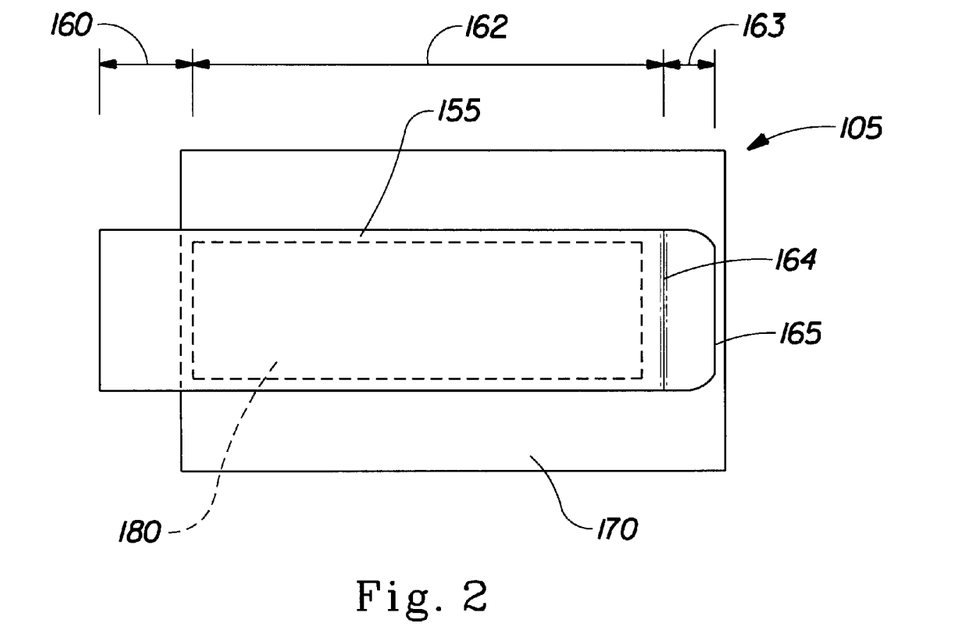
FIG. 2 is a plan view of the preferred adjustment tab.
Figure 3:
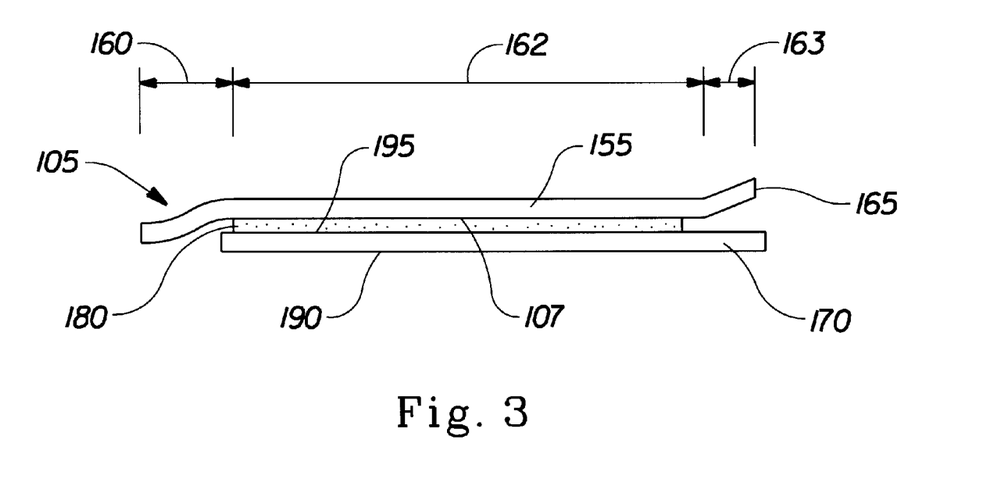
FIG. 3 is a side view of the adjustment tab in FIG. 2.

As shown in FIGS. 2 and 3, the preferred adjustment system 105 comprises an adjustment tab 155 comprising a release portion 170 on which the adjustment tab 155 is releasably attached. By "releasably attached" it is meant herein that the tab 155 can be removed from and then re-attached to the release portion 170 as many times as it suits the diaperer to more snugly fit the diaper about a wearer. The tab 155 comprises a fixed portion 160 which is fixedly attached to the absorbent article. By "fixedly attached" it is meant herein that one surface is fixed and not meant to be removed from another surface.

The fixed portion 160 is connected to an intermediate portion 162. The intermediate portion 162 is that part of the tab 155 that will be releasably attached to the release portion 170. Also, the intermediate portion 162 is connected to a grasping portion 163. Preferably, the grasping portion 163 is that part of the tab 155 which is grasped by a user. In a preferred embodiment, the grasping portion 163 is connected to the intermediate portion 162 by a fold line 164 and is thus folded upward at an angle away from the absorbent article for ready grasping by a diaperer. In addition, the grasping portion 163 preferably comprises rounded corners at its distal edge 165 to eliminate the possibility of harsh corner edges contacting the wearer's skin.

In a preferred embodiment tab 155 is releasably attached to the release portion 170 by an adhesive layer 180. The tab 155 and release portion 170 is an attachment system like those known in the art for tape tab fasteners. Exemplary adhesive tape tab fastening systems are disclosed in U.S. Pat. No. 3,848,594 entitle "Tape Fastening System For Disposable Diaper" issued to Buell on Nov. 19, 1974; and U.S. Pat. No. 4,662,875 entitled "Absorbent Article" issued to Hirotsu and Robertson on May 5, 1987.

In a preferred embodiment, the adjustment system 105 comprises a release portion 170 having a fixed surface 190 and an attachment surface 195. The adjustment tab 155 fits on and is releasably attached to the attachment surface 195 of the release portion 170. The fixed surface 190 of the release portion 170 is fixedly attached to the absorbent article 20. Preferably, the fixed surface 190 of the release portion 170 and the fixed portion 160 of the adjustment tab 155 are fixedly attached to the outer surface 52 of the backsheet 20. As shown in FIGS. 2 and 3, the adjustment tab 155 is releasably attached to the attachment surface 195 of the release portion 170 by an adhesive layer 180.

Alternatively, tab 155 is releasably attached to the release portion 170 by mechanical fasteners such as hooks and loops. In one embodiment the tab 155 may comprise a plurality of hooks while the release portion 170 comprises a plurality of loops. The tab's hooks will line up and be configured with the release portion's loops. Exemplary fastening systems comprising mechanical fastening components are described in U.S. Pat. No. 5,058,247 entitled "Mechanical Fastening Prong" issued to Thomas Oct. 22, 1991; U.S. Pat. No. 4,869,724 entitled "Mechanical Fastening Systems With Adhesive Tape Disposal Means For Disposal of Absorbent Articles" issued to Scripps on Sep. 26, 1989; and U.S. Pat. No. 4,846,815 entitled "Disposable Diaper Having an Improved Fastening Device" issued to Scripps on Jul. 11, 1989.

The adjustment tabs 155 can be disposed in the front and rear waist regions, in the crotch region, along the end edges, and along the longitudinal edges. The number of adjustment tabs 155 is not limited and can be fixed at that number and location which optimizes the desired fit, comfort and containment of the diaper. Adjustment tabs 155 are preferably placed directly on the backsheet 26, but they can also be placed on the topsheet 24 and on any other components that are attached to the backsheet 26.

Each adjustment tab 155 is preferably coupled with at least one release portion 170 in optimal locations to provide a more secure fit after placement of the diaper 20 about a wearer. However, the intermediate portion 162 of a tab 155 can also be releasably attached to the backsheet 26, while the fixed portion 160 is fixedly attached to the outer surface 52 of the backsheet 26. The adjustment tabs 155 are optimally placed as demonstrated in FIG. 1 to help provide proper closure of the diaper 20 about the waist and legs of the wearer. The preferred embodiment employs these optimally placed tape adjustment tabs 155 and release portion 170 as the primary fitting means.

Figure 4A:
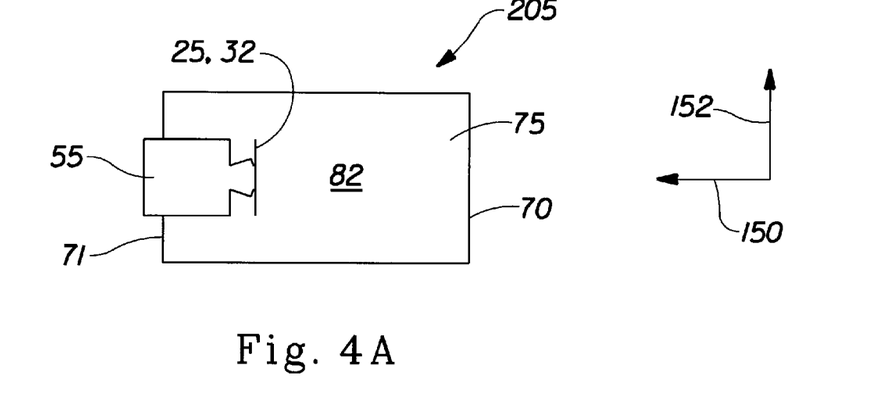
FIG. 4A is a plan view of an alternative embodiment of an adjustment system of the present invention, the outer surface of the tab facing the viewer.
Figure 4B:
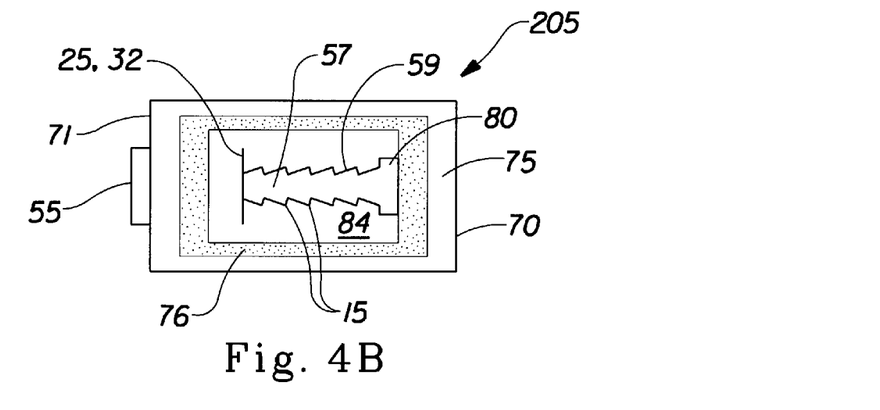
FIG. 4B is a plan view of the adjustment system shown in FIG. 4A with the inner surface of the tab facing the viewer.
Figure 4C:
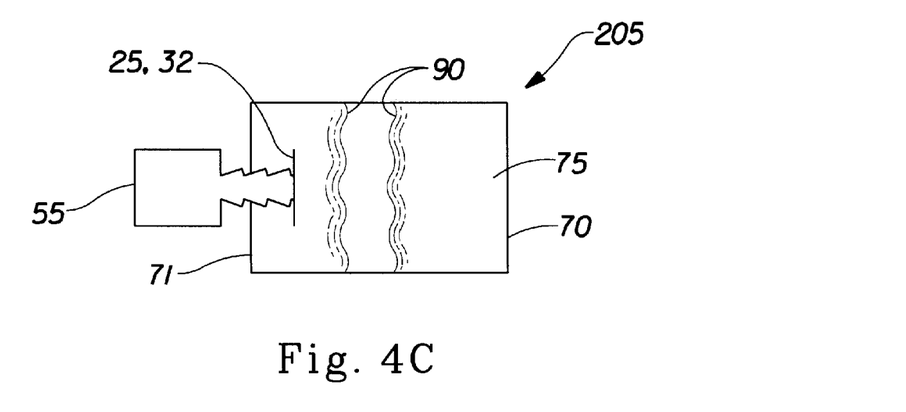
FIG. 4C is a plan view of the adjustment system of FIG. 4A showing the serrated adjusting portion and tab housing in a stressed position.

FIGS. 4A, 4B and 4C show an alternative embodiment of an adjustment system 205 which, preferably, is comprised of thermoplastic material such as polyethylene. Examples of other suitable polyethylene materials are linear low and medium polyethylene copolymers, and high density polyethylene (HIDPE). Each of these patents is incorporated herein by reference. FIGS. 4A and 4B disclose an adjustment system 205 comprising a tab housing 75 having a front end 71, a back end 70, a top surface 82, a bottom surface 84, an adhesive layer 76 preferably extending about the perimeter of the tab housing 75 bottom surface 84 and an opening 25. The adjustment system has a longitudinal axis 150 and a transverse axis 152. FIG. 4A shows the portion of the adjustment system 205 which is that surface which preferably faces out from the outer surface 52 of the backsheet 26. FIG. 4B shows the bottom surface 84 of the system 205 in FIG. 4A, which surface is preferably fixedly attached to the outer surface 52 of the backsheet 26 of the diaper 20. The adhesive layer 76 preferably comprises adhesives which provide fixed attachment to the backsheet material (i.e., thermoplastic film) and are of necessary strength to hold the backsheet when the tab housing 75 is in a tensioned or contracted condition, such as illustrated in FIG. 4C. Suitable adhesives include any of those known by one of ordinary skill in the art for securing polyethylene films and polymers.

In the embodiment shown in FIGS. 4A, 4B, and 4C, the adjustment system 205 additionally comprises an adjusting portion 57. The adjusting portion 57 comprises a rear end 80, an serrated extension member 59 connected to the rear end 80, and a head portion connected to the extension member 59. The rear end 80 is attached adjacent to the tab housing back end 70, the attachment surface to the tab housing 75 (e.g., the outer surface 52 of the backsheet 26), or both. The extension member 59 extends from the adjusting portion's rear end 80 through the opening 25 to its head portion 55. The tab housing 75 is constricted by pulling the head portion 55 in a direction along the longitudinal axis 150. The adjusting portion 57 can be of any suitable geometry which maintains constriction or lines of tension 90 (FIG. 4C) in the tab housing 75. These lines of tension 90 indicate that the portion of the diaper which is fixedly attached to the diaper is also constricted or under tension. The head portion 55 is preferably broad and flat and preferably remains on the top surface 82 of the tab housing 75. FIG. 4C shows that lines of tension 90 can form as a result of the tab 55 being pulled in a direction away from the tab housing 75 along the longitudinal axis 150. The thermoplastic backsheet material moves in the direction of the force applied causing a more conforming fit about the wearer. As shown, this fit is maintained by the action of the outer tip ends 15 of the serrated adjusting portion 57 acting against the cross-sectional edges 32 of the opening 25, which at a point of desired adjustment by the diaperer, remain mechanically positioned against the cross-sectional opening 25; i.e., the last serrated adjusting portion 57 moved through the opening 25 will remain fixed against that opening 25 (i.e., an edge 32) at the point of desired adjustment, thus keeping the tab housing 75 in a tensioned state.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a first waist region, a second waist region longitudinally opposed to said first waist region, a crotch region positioned between said first waist region and said second waist region, longitudinal edges, end edges, an outer surface, and an inner surface, said absorbent article comprising:

a containment assembly comprising a liquid pervious topsheet, a liquid impervious backsheet joined to said topsheet, and an absorbent core positioned between said topsheet and said backsheet and a pair of elasticized gasketing leg cuffs in the crotch region;

a fastening system disposed on the absorbent article for providing a side closure which maintains the first waist region and the second waist region in an overlapping configuration, the fastening system comprising a securement member disposed adjacent each of the longitudinal edges in the second waist region and a landing member disposed in the first waist region, said landing member being engageable with said securement members; and an adjustment system including a pair of adjustment tabs disposed adjacent to each longitudinal edge and oriented in a non-parallel relation to the end edge of the article, each said adjustment tab having a fixed portion secured to the outer surface of the article in the first waist region or the crotch region, an intermediate portion connected to said fixed portion and being releasably attachable to the outer surface of the article, and a grasping portion connected to said intermediate portion, said adjustment system being adapted to provide an improved fit about a wearer's leg when said intermediate portion is releasably attached to the outer surface of the article in the first waist region or the crotch region.

2. The absorbent article of claim 1 wherein said intermediate portion and said grasping portion are connected by a fold line, said grasping portion being folded upward away from the outer surface.

3. The absorbent article of claim 1 wherein at least one of said adjustment tabs is disposed in the first waist region.

4. The absorbent article of claim 1 wherein said adjustment system further comprises a release portion having a fixed surface opposed to an attachment surface, at least one of said adjustment tabs being releasably attached to said attachment surface of said release portion.

5. The absorbent article of claim 1 wherein said fixed surface of said release portion and said fixed portion of said at least one of said adjustment tabs are fixedly attached to said backsheet.

6. The absorbent article of claim 4 wherein said at least one of said adjustment tabs and said release portion are releasably attached to one-another by an adhesive layer.

7. The absorbent article of claim 4 wherein said at least one of said adjustment tabs and said release portion are releasably attached to one-another by hooks and loops.

8. The absorbent article of claim 1 wherein the first waist region is a front waist region.

9. The absorbent article of claim 1 wherein the first waist region is a rear waist region.

10. The absorbent article of claim 1 wherein said adjustment system further comprises a third adjustment tab disposed in the second waist region, said third adjustment tab having a third fixed portion secured to the outer surface of the article in the second waist region, a third intermediate portion connected to said third fixed portion, said third intermediate portion being releasably attachable to the outer surface of the article in the second waist region to provide an improved fit about a waist of a wearer.

11. The absorbent article of claim 23 wherein said third adjustment tab is oriented generally parallel to the end edge of the absorbent article.

* * * * *